(12) United States Patent
Hu

(10) Patent No.: US 9,645,499 B2
(45) Date of Patent: May 9, 2017

(54) PHOTORESIST WITH TOP-COATING PHOTO-DECOMPOSABLE BASE FOR PHOTOLITHOGRAPHY

(71) Applicant: SEMICONDUCTOR MANUFACTURING INTERNATIONAL (SHANGHAI) CORPORATION, Shanghai (CN)

(72) Inventor: Huayong Hu, Shanghai (CN)

(73) Assignee: Semiconductor Manufacturing International (Shanghai) Corporation, Shanghai (CN)

( * ) Notice: Subject to any disclaimer, the term of this patent is extended or adjusted under 35 U.S.C. 154(b) by 0 days.

(21) Appl. No.: 14/833,029

(22) Filed: Aug. 21, 2015

(65) Prior Publication Data

US 2016/0062241 A1 Mar. 3, 2016

(30) Foreign Application Priority Data

Aug. 28, 2014 (CN) .......................... 2014 1 0432069

(51) Int. Cl.
| | |
|---|---|
| G03F 7/004 | (2006.01) |
| G03F 7/11 | (2006.01) |
| G03F 7/32 | (2006.01) |
| G03F 7/09 | (2006.01) |
| G03F 7/20 | (2006.01) |

(Continued)

(52) U.S. Cl.
CPC .............. *G03F 7/325* (2013.01); *C07C 51/00* (2013.01); *C07C 51/14* (2013.01); *C07C 55/08* (2013.01); *C07C 55/12* (2013.01); *C07C 55/14* (2013.01); *C07C 55/32* (2013.01); *C07C 59/21* (2013.01); *C07C 59/295* (2013.01); *C07C 59/315* (2013.01); *C07C 59/347* (2013.01); *C07C 229/24* (2013.01); *G03F 7/0045* (2013.01);

(Continued)

(58) Field of Classification Search
CPC . G03F 7/004; G03F 7/32; G03F 7/325; G03F 7/027; G03F 7/11; G03F 7/20; C07C 51/00; C07C 51/14; C07C 59/315; C07C 59/21; C07C 59/32; C07C 59/295; C07C 59/347; C07C 55/32; C07C 55/14; C07C 55/08; C07C 55/12; C07C 229/24
USPC ...... 430/270.1, 271.1, 273.1, 322, 325, 329, 430/330, 434, 435, 913; 562/583, 577, 562/596, 582, 578, 571, 594, 568
See application file for complete search history.

(56) References Cited

U.S. PATENT DOCUMENTS

| | | | |
|---|---|---|---|
| 7,507,518 B2 * | 3/2009 | Fujita .................... | G03F 7/0045 430/157 |
| 9,244,347 B2 * | 1/2016 | Komuro ................ | C07C 381/12 |

(Continued)

*Primary Examiner* — Amanda C Walke
(74) *Attorney, Agent, or Firm* — Kilpatrick Townsend and Stockton LLP

(57) ABSTRACT

A lithographic method includes forming a photoresist layer on a target layer, forming a photo-decomposable base (PDB) layer on the photo resist layer, performing an exposure operation using a mask, and performing a negative development treatment to form a patterned photoresist layer on the target layer. In some cases, the photo-decomposable base layer includes a self-generating top coating photo-decomposable base (TC-PDB) layer. The method can also include forming a top surface water-resistant coating in separate coating process. In some embodiments, a top surface water-resistant coating is self-generated during a photoresist coating process.

15 Claims, 5 Drawing Sheets

(51) Int. Cl.
| | |
|---|---|
| *C07C 59/347* | (2006.01) |
| *C07C 59/295* | (2006.01) |
| *C07C 51/14* | (2006.01) |
| *C07C 59/21* | (2006.01) |
| *C07C 55/32* | (2006.01) |
| *C07C 51/00* | (2006.01) |
| *C07C 59/315* | (2006.01) |
| *C07C 55/08* | (2006.01) |
| *C07C 229/24* | (2006.01) |
| *C07C 55/14* | (2006.01) |
| *C07C 55/12* | (2006.01) |
| *G03F 7/095* | (2006.01) |

(52) U.S. Cl.
CPC .............. *G03F 7/091* (2013.01); *G03F 7/095* (2013.01); *G03F 7/11* (2013.01); *G03F 7/20* (2013.01)

(56) References Cited

U.S. PATENT DOCUMENTS

| | | | | |
|---|---|---|---|---|
| 2003/0017411 | A1* | 1/2003 | Shimada | B41C 1/1008 430/270.1 |
| 2006/0078823 | A1* | 4/2006 | Kanda | G03F 7/0046 430/270.1 |
| 2007/0148595 | A1* | 6/2007 | Kanda | G03F 7/0395 430/270.1 |
| 2009/0163653 | A1* | 6/2009 | Takagi | C07C 51/41 524/777 |
| 2009/0239176 | A1* | 9/2009 | Kanda | G03F 7/0046 430/285.1 |
| 2013/0052585 | A1* | 2/2013 | Ayothi | C07D 241/04 430/283.1 |
| 2013/0230813 | A1* | 9/2013 | McBrien | G01L 19/0654 432/1 |
| 2014/0377707 | A9* | 12/2014 | Minegishi | C08F 214/18 430/325 |

\* cited by examiner

PHOTORESIST WITH TOP-COATING PHOTO-DECOMPOSABLE BASE FOR PHOTOLITHOGRAPHY

CROSS-REFERENCES TO RELATED APPLICATIONS

This application claims priority to Chinese patent application No. 201410432069.1, filed on Aug. 28, 2014, the content of which is incorporated herein by reference in its entirety.

BACKGROUND OF THE INVENTION

The present invention relates to semiconductor technologies, and more particularly to photolithography techniques for the fabrication of semiconductor devices.

In the field of semiconductor technology, the positive tone develop (PTD) technology uses TMAH (Tetramethylammonium hydroxide) to dissolve photoresist in the exposed areas. In contrast, in negative tone develop (NTD) technology, an organic solvent is used to dissolve away the photoresist in regions that have not been exposed. Negative tone develop (NTD) technology can improve small pitch resolution and has relatively broad application prospects.

However, the inventor has identified certain limitations in conventional negative tone develop (NTD) technology as explained below. FIGS. 1A to 1C are cross-sectional view diagrams illustrating a conventional lithographic method, which includes the following steps:

Step E1: On a film 100 that is to be etched, sequentially form the following layers: a bottom anti-reflective coating layer (BARC) 101, a positive resist layer 102, and a water-resistant top coating (TC) layer 103, as shown in FIG. 1A;

Step E2: Using a mask plate 600 to perform an exposure process on positive photoresist layer 102, forming exposed areas 10201 and non-exposed areas 10202, as shown in FIG. 1B;

Step E3: Perform a negative development treatment to form a patterned photoresist 1021 to be used as a mask, as shown in FIG. 1C.

Patterned photoresist 1021 formed as described above will often exhibit a T-shaped profile, i.e., the top portion of the patterned photoresist is wider than the bottom portion. The presence of the T-top defects can reduce the ability of negative development technology (NTD) to achieve a small pitch. Various methods have been proposed to solve the T-top defect issue, such as changing the solvent DEV, improved optical contrast (NILS), changing the negative photoresist component, and the like. However, these conventional solutions are not satisfactory. Therefore, in order to solve this technical problem, an improved lithographic method is needed.

BRIEF SUMMARY OF THE INVENTION

Embodiments of the present invention provide lithography methods for manufacturing a semiconductor device structure at increasingly small dimensions.

According to some embodiments of the invention, a lithographic method includes forming a photoresist layer on a target layer, forming a photo-decomposable base (PDB) layer on the photo resist layer, performing an exposure operation using a mask, and performing a negative development treatment to form a patterned photoresist layer on the target layer.

In some embodiments of the above method, the photo-decomposable base layer includes a self-generating top coating photo-decomposable base (TC-PDB) layer. In some embodiments, the method also includes forming a top surface water-resistant coating in a separate coating process. In some embodiments, a top surface water-resistant coating is self-generated during a photoresist coating process.

In some embodiments, the photo-decomposable base layer includes a fluorinated monocarboxylate cation photo-decomposable base or a fluorinated dicarboxylate cation photo-decomposable base. In some embodiments, forming a photo-decomposable base (PDB) layer includes using a coating method. In some embodiments, forming a photoresist layer includes coating a positive photoresist layer, and the positive photoresist layer includes photo-acid generator (PAG), resist additives, and solvents. In some embodiments, the photo acid generator can include onium salts, aromatic diazonium salts, sulfonium salts, diaryliodonium salts, dodecane sulfonate of N-hydroxy-naphthalimide, and one or more of sulfonic acid esters in N-hydroxyamides. In some embodiments, the method also includes forming a bottom antireflective coating layer before forming the photoresist layer.

In some embodiments, a lithographic method includes forming a composite layer on a target layer. The composite layer includes a photo-decomposable base (PDB) layer over a photo resist layer. The method also includes performing an exposure operation using a mask, and performing a negative development treatment to form a patterned photoresist layer on the target layer. In an embodiment, forming a composite layer on a target layer includes forming a photoresist layer on the target layer, and forming a photo-decomposable base (PDB) layer over the photo resist layer. In some embodiments, the photo-decomposable base (PDB) layer can be patterned, as shown in the example in FIG. 2A. In other embodiments, the photo-decomposable base (PDB) layer is not patterned. In another embodiment, forming a composite layer on a target layer includes using a coating process to form a photoresist layer, which includes a photo-decomposable base (PDB) material, which can form a top coating photo-decomposable base layer during the coating or exposure process. In some embodiments, the method also includes forming a top surface water-resistant coating in a separate coating process. In some embodiments, a top surface water-resistant coating is self-generated during a photoresist coating process.

The following description, together with the accompanying drawings, will provide a better understanding of the nature and advantages of the claimed invention.

DETAILED DESCRIPTION OF THE INVENTION

Figure 1A:
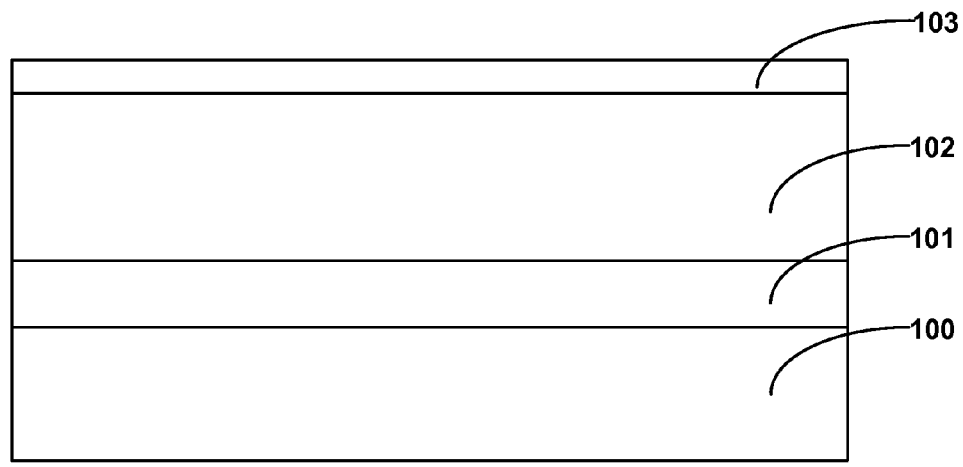
FIG. 1A is a cross-sectional view diagram illustrating a conventional lithographic method.
Figure 1B:
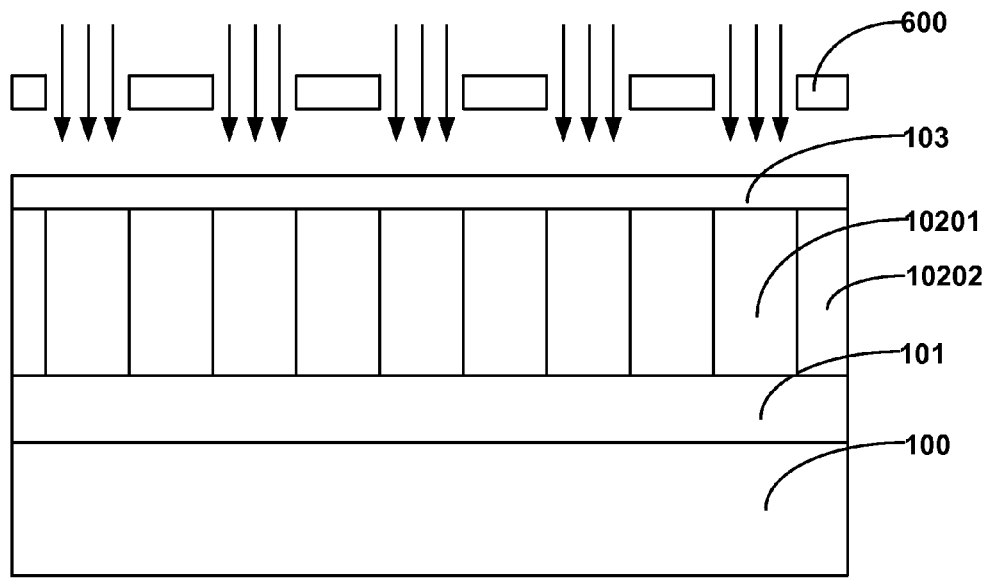
FIG. 1B is a cross-sectional view diagram illustrating a conventional lithographic method.
Figure 1C:
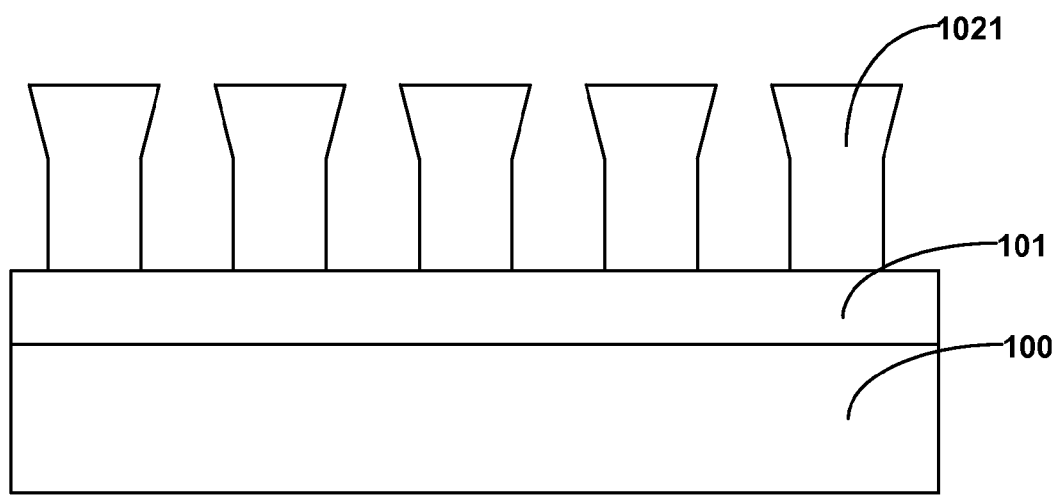
FIG. 1C is a cross-sectional view diagram illustrating a conventional lithographic method.

Embodiments of the present invention are related to techniques for using a negative developer (NTD) photolithography method with improved small pitch performance.

In the following description, numerous specific details are provided for a thorough understanding of the present invention. However, it should be appreciated by those of skill in the art that the present invention may be realized without one or more of these details. In other examples, features and techniques known in the art will not be described for purposes of brevity.

It should be understood that the drawings are not drawn to scale, and similar reference numbers are used for representing similar elements. Embodiments of the invention are described herein with reference to cross-section illustrations that are schematic illustrations of idealized embodiments (and intermediate structures) of the invention. The thickness of layers and regions in the drawings may be exaggerated relative to each other for clarity. Additionally, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

It will be understood that, when an element or layer is referred to as "on," "disposed on," "adjacent to," "connected to," or "coupled to" another element or layer, it can be disposed directly on the other element or layer, adjacent to, connected or coupled to the other element or layer, or intervening elements or layers may also be present. In contrast, when an element is referred to as being "directly on," directly disposed on," "directly connected to," or "directly coupled to" another element or layer, there are no intervening elements or layers present between them. It will be understood that, although the terms "first," "second," "third," etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Relative terms, or spatial relationship terms, such as "under," "below," "underneath," "over," "on," "above," "bottom," and "top" are used herein to described a relationship of one element, layer or region to another element, layer or region as illustrated in the figures. It will be understood that these terms are intended to encompass different orientations of the structure in addition to the orientation depicted in the figures. For example, if the device shown in the figures is flipped, the description of an element being "below" or "underneath" another element would then be oriented as "above" the other element. Therefore, the term "below," "under," or "underneath" can encompass both orientations of the device. Because devices or components of embodiments of the present invention can be positioned in a number of different orientations (e.g., rotated 90 degrees or at other orientations), the relative terms should be interpreted accordingly.

The terms "a", "an" and "the" may include singular and plural references. It will be further understood that the terms "comprising", "including", "having" and variants thereof, when used in this specification, specify the presence of stated features, steps, operations, elements, and/or components, but do not preclude the presence or addition of one or more other features, steps, operations, elements, components, and/or groups thereof. Furthermore, as used herein, the words "and/or" may refer to and encompass any possible combinations of one or more of the associated listed items.

The use of the terms first, second, etc. do not denote any order, but rather the terms first, second, etc. are used to distinguish one element from another. Furthermore, the use of the terms a, an, etc. does not denote a limitation of quantity, but rather denote the presence of at least one of the referenced items.

The term "vertical" as used in this application is defined as a plane perpendicular to the conventional plane or surface of a wafer or substrate, regardless of the orientation of the wafer or substrate. The term "horizontal" refers to a direction perpendicular to the vertical as defined above.

Embodiments of the invention are described herein with reference to cross-section illustrations that are schematic illustrations of idealized embodiments (and intermediate structures) of the invention. The thickness of layers and regions in the drawings may be exaggerated for clarity. Additionally, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a discrete change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the invention.

Prepositions, such as "on", "side" (as in "sidewall"), "below", "above", "higher", "lower", "over" and "under" are defined with respect to the conventional plane or surface being on the top surface of the wafer or substrate, regardless of the orientation of the wafer or substrate. It will be understood that these terms are intended to encompass different orientations of the device in addition to the orientation depicted in the figures.

Figure 2A:
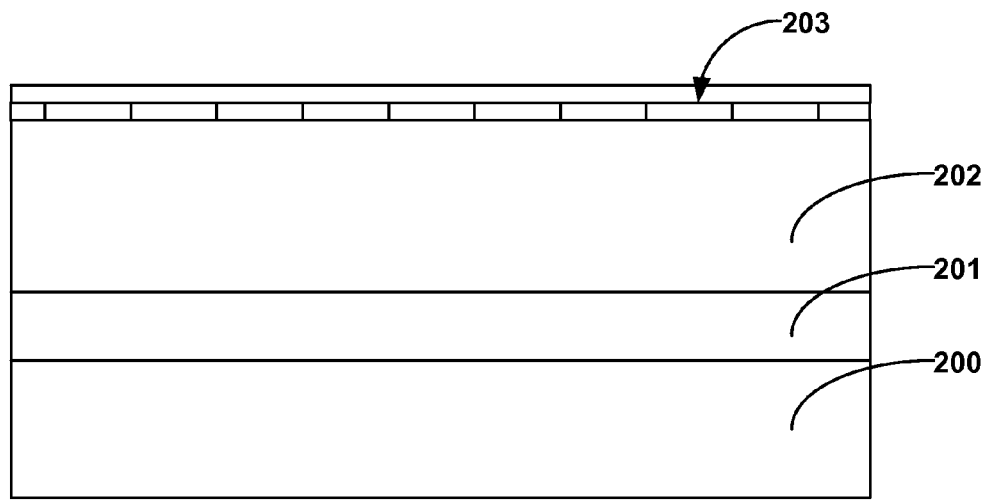
FIG. 2A is a cross-sectional view diagram illustrating a lithographic method according to an embodiment of the present invention.
Figure 2B:
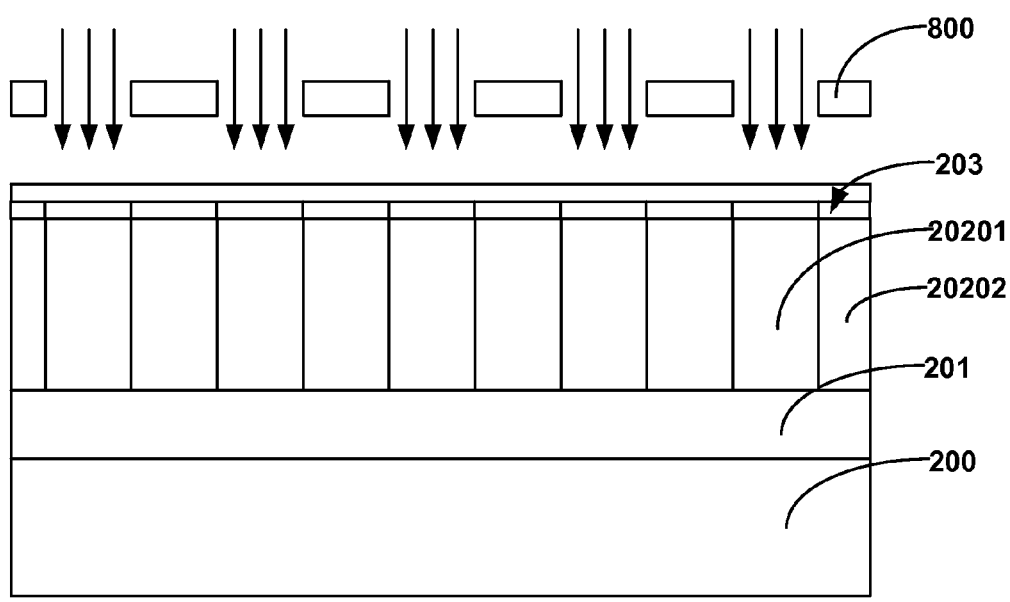
FIG. 2B is a cross-sectional view diagram illustrating a lithographic method according to an embodiment of the present invention.
Figure 2C:
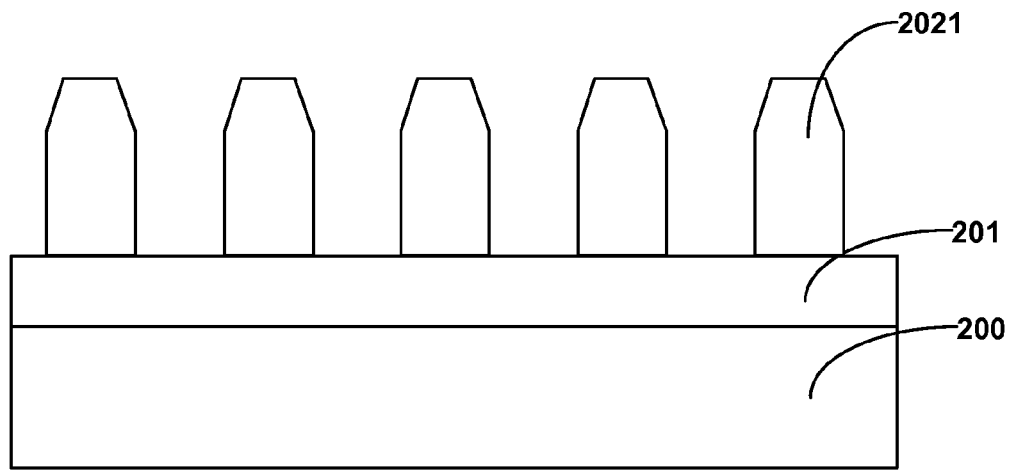
FIG. 2C is a cross-sectional view diagram illustrating a lithographic method according to an embodiment of the present invention.
Figure 2C:
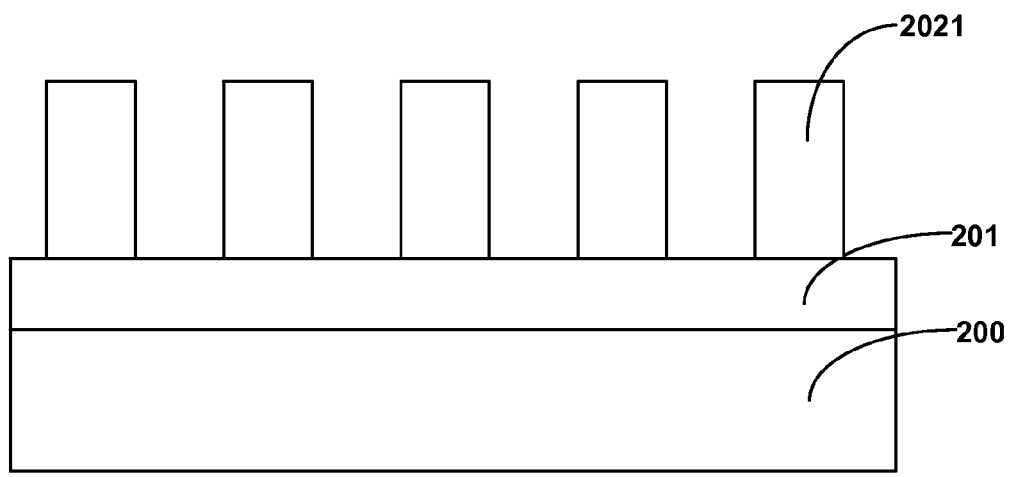

FIGS. 2A to 2C are cross-sectional view diagrams illustrating a lithographic method according to an embodiment of the present invention. The method includes the following processes.

Step A1: On a layer 200 that is to be etched, sequentially form the following layers: a bottom anti-reflective coating layer (BARC) 201, a positive photo resist layer 202, and a photo-decomposable base layer 203, as shown in FIG. 2A;

Step A2: Using a mask plate 800 to perform an exposure process on positive photoresist layer 202, forming exposed areas 20201 and non-exposed areas 20202, as shown in FIG. 2B;

Step A3: Perform negative development treatment to form a patterned photoresist 2021 to be used as a mask, as shown in FIG. 2C or 2C'.

As shown in FIG. 2A, bottom anti-reflective coating layer (BARC) 201, positive photo resist layer 202, and photo-decomposable base layer 203 are sequentially formed on layer 200. Layer 200 is also referred to as a target layer, and may be one of a variety of films involved in the semiconductor device manufacturing process, e.g., a gate material layer, a metal layer, an interlayer dielectric layer, and the like. Layer 200 may be etched to form a patterned layer or may receive ion implantation in selected regions. The method described here can be applied to any layer to be etched or implanted. In FIG. 2A, bottom anti-reflective coating layer (BARC) 201 is used to reduce the effect of reflection from the lower surface of the photoresist during exposure, so that most of the exposure energy is absorbed by the photoresist. In this embodiment, the bottom anti-reflective layer 201 may use a variety of suitable materials. Further, in some embodiments, the bottom anti-reflective layer 201 may be omitted.

In embodiments of the invention, positive resist layer 202 can be formed by a photo resist coating method, such as spin coating, or other methods may be used. Positive photoresist layer 202 may include photo-acid generator (PAG), resist additives, and solvents. The photo acid generator can include onium salts, aromatic diazonium salts, sulfonium salts, diaryliodonium salts, dodecane sulfonate of N-hydroxy-naphthalimide, and one or more of sulfonic acid esters in N-hydroxyamides, etc.

In embodiments of the invention, positive photoresist layer 202 and photo-decomposable base layer 203 can be formed using a conventional photo resist coating method. In some embodiments, the photo-decomposable base (PDB) layer can be patterned, as shown in the example in FIG. 2A. In other embodiments, the photo-decomposable base (PDB) layer is not patterned. In another embodiment, a coating process forms a photoresist layer, which includes a photo-decomposable base (PDB) material, which can form a top coating photo-decomposable base layer during a coating or an exposure process.

Photo-decomposable base layer 203 can include a photo-decomposable base, a photo acid generator, photoresist additives, and solvents. Photo-decomposable base layer 203 can be self-generating top coating photo-decomposable base (TC-PDB) at the time of coating, or ordinary photo decomposable base (PDB). Photo-decomposable base layer 203 includes alkaline substances. After positive resist layer 202 is exposed, the light at the surface can decompose portions of base layer 203 located in unexposed areas to provide alkaline substances to prevent the diffusion of the photo acid. Thus, the higher base concentration at the top of unexposed regions can prevent acid diffusion into the top portions of the unexposed regions, and can help improve the T-top profile after photo resist development.

In embodiments of the invention, the self-generating top coating photo-decomposable base (TC-PDB) can include fluorinated monocarboxylate cation photo-decomposable base or fluorinated dicarboxylate cation photo-decomposable base. These components can obtain enough separation energy to enable self-generated topcoat photo-decomposable base to rise to the top surface of the photo resist system.

In an embodiment, the self-generating top coating photo-decomposable base (TC-PDB) can include a compound of the following structure.

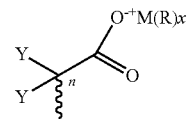

In the above composition, Y is fluorine (F), M is selected from sulfur (S), or iodine (I), R is selected from hydrogen (H), hydroxyl, carboxyls, amines, alkyls, alkylenes, aryls, and arylenes. When x is equal to 2, M is iodine (I), and when x is equal to 3, M is sulfur (S). n is a natural number, which ranges from 6-100.

In another embodiment, the self-generating top coating photo-decomposable base (TC-PDB) can include a compound of the following structure.

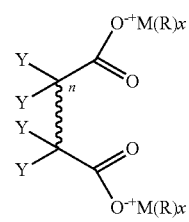

In the above composition, Y is fluorine (F). M is selected from sulfur (S), or iodine (I). R is selected from hydrogen (H), hydroxyl, carboxyls, amines, alkyls, alkylenes, aryls, and arylenes. When x is equal to 2, M is iodine (I), and when x is equal to 3, M is sulfur (S). n is a natural number, which ranges from 6-100.

In a third embodiment, the self-generating top coating photo-decomposable base (TC-PDB) can include a compound of the following structure.

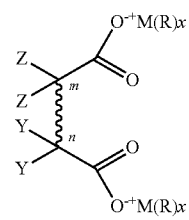

In the above composition, Y is fluorine (F). M is selected from sulfur (S), or iodine (I). R is selected from hydrogen (H), hydroxyl, carboxyls, amines, alkyls, alkylenes, aryls, and arylenes. When x is equal to 2, M is iodine (I), and when x is equal to 3, M is sulfur (S). n is a natural number, which ranges from 6-100.

In some embodiments, the self-generating top coating photo-decomposable base (TC-PDB) can include one or more of the following compounds.

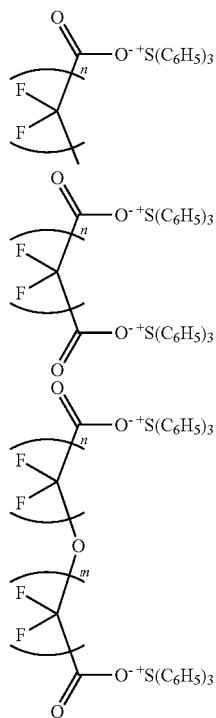

As shown in FIG. 2B, an exposure process is performed on positive photoresist layer 202 using a mask plate 800 to form exposed areas 20201 and non-exposed areas 20202. The mask 800 can be one of a variety of possible masks. The transparent region in mask 800 corresponds to the areas intended to be retained in layer 200. During the exposure process, the surface of the exposed portion of photo-decomposable base layer 203 will go through certain reactions. For example, in the exposure process, alkaline materials in exposed areas of photo-decomposable base layer 203 are decomposed.

The inventor's research has found that the T-shaped top portions of patterned photoresist are caused by the diffusion of acid produced in the exposed areas of the photoresist into the non-exposed areas. In embodiments of the invention, since photo-decomposable base layer 203 can be decomposed by surface light to produce alkaline materials to prevent the acid generated in the exposed areas from moving to the non-exposed areas, T-top defects are thereby prevented in the patterned photoresist.

As shown in FIG. 2C or 2C', a negative development treatment is performed to form a patterned photoresist 2021 to be used as a mask. In the process of negative development process, organic solvents can be used to dissolve the unexposed areas of the photoresist. Patterned photoresist 2021 can be used as a mask for subsequent etching or ion implantation. As described above, the alkaline materials produced by the decomposition of photo-decomposable base layer 203 prevents the acid from the exposed areas from moving to unexposed areas to prevent the T-shaped defects in resist profile. In other words, the width of the top portion is not less than the width of the bottom portion. In one example, FIG. 2C shows a cross-sectional view of a patterned photoresist 202, which is slightly narrower at the rounded top than the bottom portion. In another example, FIG. 2C' shows a cross-sectional view of a patterned photoresist 202, whose profile is substantially a vertical shape, with an approximately rectangular cross-section. In both FIGS. 2C and 2C', the T-shaped wide top portion is absent. The difference between the profiles in FIGS. 2C and 2C' is caused by variations of the material, thickness, etc., of the photo-decomposable base layer 203.

Figure 3:
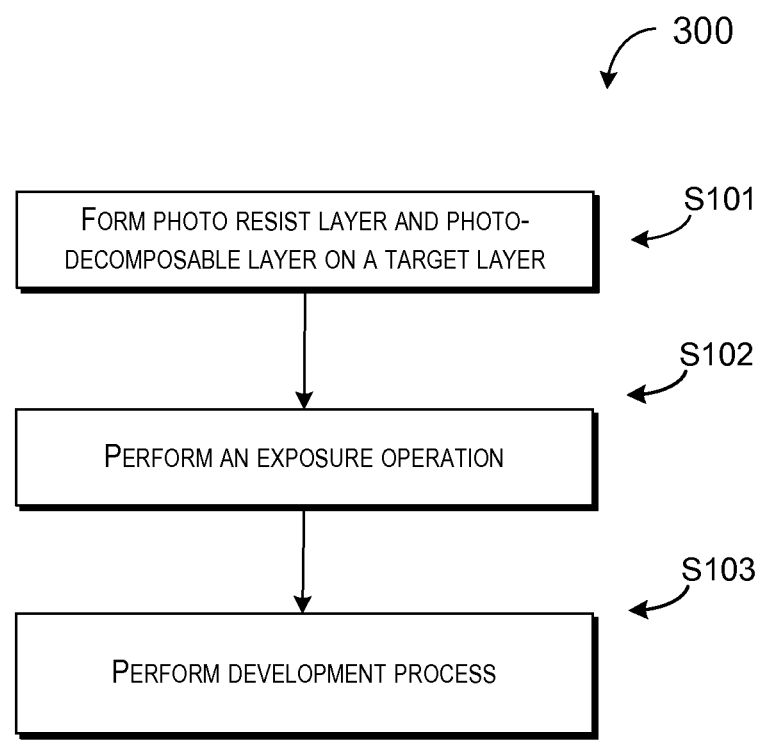
FIG. 3 is a simplified flow chart illustrating a lithographic method according to an embodiment of the present invention.

FIG. 3 is a simplified flow chart illustrating a lithographic method according to one embodiment of the present invention. As shown in FIG. 3, method 300 includes the following processes.

S101: Form a photo resist layer and a photo-decomposable base layer on a target layer;

S102: Perform an exposure operation using a mask; and

S103: Perform a negative development treatment to form a patterned photoresist.

In some embodiments, a lithographic method includes forming a composite layer on a target layer. The composite layer includes a photo-decomposable base (PDB) layer over a photo resist layer. The method also includes performing an exposure operation using a mask, and performing a negative development treatment to form a patterned photoresist layer on the target layer. In an embodiment, forming a composite layer on a target layer includes forming a photoresist layer on the target layer, and forming a photo-decomposable base (PDB) layer over the photo resist layer. In some embodiment, the photo-decomposable base (PDB) layer can be patterned, as shown in the example in FIG. 2A. In other embodiments, the photo-decomposable base (PDB) layer is not patterned. In another embodiment, forming a composite layer on a target layer includes using a coating process to form a photoresist layer, which includes a photo-decomposable base (PDB) material, which can form a top coating photo-decomposable base layer during the coating or exposure process. In some embodiments, the method also includes forming a top surface water-resistant coating in a separate coating process. In some embodiments, a top surface water-resistant coating is self-generated during a photoresist coating process.

While the present invention is described herein with reference to illustrative embodiments, this description is not intended to be construed in a limiting sense. Rather, the purpose of the illustrative embodiments is to make the spirit of the present invention be better understood by those skilled in the art. In order not to obscure the scope of the invention, many details of well-known processes and manufacturing techniques are omitted. Various modifications of the illustrative embodiments as well as other embodiments will be apparent to those of skill in the art upon reference to the description. For example, although certain composition structures and examples of the photo-decomposable base layer are described, it is understood that the other materials of similar properties can also be used. It is therefore intended that the appended claims encompass any such modifications.

Furthermore, some of the features of the preferred embodiments of the present invention could be used to advantage without the corresponding use of other features. As such, the foregoing description should be considered as merely illustrative of the principles of the invention, and not in limitation thereof.

What is claimed is:

1. A lithographic method, comprising:
   forming a photoresist layer on a target layer;
   forming a photo-decomposable base (PDB) layer on the photo resist layer;
   performing an exposure operation using a mask exposing a region of the PDB layer so that a top surface of an exposed region of the PDB layer has a base concentration higher than a base of the exposed region of the PDB layer; and performing a negative development process to form a patterned photoresist layer on the target layer.

2. The method of claim 1, wherein the photo-decomposable base layer comprises a self-generating top coating photo-decomposable base (TC-PDB) layer.

3. The method of claim 1, further comprising forming a top surface water-resistant coating in a separate coating process.

4. The method of claim 1, wherein a top surface water-resistant coating is self-generated during a photoresist coating process.

5. The method of claim 1, wherein the photo-decomposable base layer comprises a fluorinated monocarboxylate cation photo-decomposable base or a fluorinated dicarboxylate cation photo-decomposable base.

6. The method of claim 1, wherein forming a photo-decomposable base (PDB) layer comprises a coating method.

7. The method of claim 1, wherein forming a photoresist layer comprises coating a positive photoresist layer, the positive photoresist layer including photo-acid generator (PAG), resist additives, and solvents.

8. The method of claim 7, wherein the photo acid generator can include onium salts, aromatic diazonium salts, sulfonium salts, diaryliodonium salts, dodecane sulfonate of N-hydroxy-naphthalimide, and one or more of sulfonic acid esters in N-hydroxyamides.

9. The method of claim 1, further comprising forming a bottom antireflective coating layer before forming the photoresist layer.

10. A lithographic method, comprising:

forming a composite layer on a target layer, the composite layer including a photo-decomposable base (PDB) layer over a photo resist layer;

performing an exposure operation using a mask exposing a region of the PDB layer so that a top surface of an exposed region of the PDB layer has a base concentration higher than a base of the exposed region of the PDB layer; and performing a negative development treatment to form a patterned photoresist layer on the target layer.

11. The method of claim 10, wherein forming a composite layer on a target layer comprises:

forming a photoresist layer on the target layer; and forming a photo-decomposable base (PDB) layer over the photo resist layer.

12. The method of claim 11, wherein the photo-decomposable base (PDB) layer is patterned.

13. The method of claim 10, wherein forming a composite layer on a target layer comprises:

forming a photoresist layer using a coating process, the photoresist layer including a photo-decomposable base (PDB) material; and forming a top coating photo-decomposable base layer during a coating or an exposure process.

14. The method of claim 10, further comprising forming a top surface water-resistant coating in a separate coating process.

15. The method of claim 10, wherein a top surface water-resistant coating is self-generated during a photoresist coating process.

* * * * *